United States Patent
Brown et al.

(10) Patent No.: US 6,436,879 B1
(45) Date of Patent: Aug. 20, 2002

(54) PROCESS FOR PRODUCING A PREDETERMINED CESIUM COMPOUND

(75) Inventors: Patrick M. Brown, Exton; Michael C. Northrup, Boyertown, both of PA (US); Bart F. Bakke, Manitoba (CA)

(73) Assignee: Cabot Corporation, Boston, MA (US)

( * ) Notice: Subject to any disclaimer, the term of this patent is extended or adjusted under 35 U.S.C. 154(b) by 0 days.

(21) Appl. No.: 09/470,803

(22) Filed: Dec. 22, 1999

Related U.S. Application Data (63) Continuation of application No. 08/858,758, filed on May 19, 1997, now Pat. No. 6,015,535, which is a continuation of application No. 08/417,562, filed on Apr. 6, 1995, now abandoned.

(51) Int. Cl.[7] .............................................. C09K 7/02
(52) U.S. Cl. ..................... 507/145; 507/140; 507/103
(58) Field of Search ............................... 507/140, 145, 507/103

(56) References Cited

U.S. PATENT DOCUMENTS

| | | |
|---|---|---|
| 675,686 A | 6/1901 | Vis |
| 2,030,777 A | 2/1936 | Woods |
| 2,234,790 A | 3/1941 | Zacher |
| 2,238,671 A | 4/1941 | Woodhouse |
| 2,301,875 A | 11/1942 | Holmes |
| 2,474,330 A | 6/1949 | Salathiel |
| 2,481,455 A | 9/1949 | Stenger |
| 2,571,093 A | 10/1951 | Temple |
| 2,640,810 A | 6/1953 | Cardwell et al. |
| 2,731,414 A | 1/1956 | Binder, Jr. et al. |
| 2,771,420 A | 11/1956 | Rowe |
| 3,000,818 A | 9/1961 | Abbott, Jr. |
| 3,112,169 A | 11/1963 | Berthold et al. |

(List continued on next page.)

FOREIGN PATENT DOCUMENTS

| | | |
|---|---|---|
| AU | B-78249/87 | 3/1988 |
| CA | 1295120 | 2/1992 |

(List continued on next page.)

OTHER PUBLICATIONS

Downs, J. D. Et Al., Development of Environmentally Benign Formate–Based Drilling and Completion Fluids, SPE 27143, pp. 419–428, Jan. 1994.*

Slim Holes Fat Savings, Journal of Petroleum Technology, vol. 45, No. 9, pp. 816–819, Sep. 1993.*

(List continued on next page.)

*Primary Examiner*—Philip Tucker (57) ABSTRACT

Disclosed is a method for producing a predetermined cesium compound. The method comprises treating a cesium-containing material with a suitable reagent to dissolve at least a portion of the cesium contained in the material and form a slurry; adding a base comprising slaked lime or calcium carbonate and an acid containing the anion of the predetermined cesium compound to the slurry comprising the dissolved cesium; and separating the predetermined cesium compound. In one embodiment of the invention there is provided a method for producing a predetermined cesium compound from an ore comprising cesium aluminosilicate comprising: treating an ore comprising cesium aluminosilicate with an acid to form a slurry and dissolve at least a portion of the cesium contained in the ore; adding a base comprising slaked lime or calcium carbonate and a quantity of an acid containing the anion of the predetermined cesium compound to the slurry comprising dissolved or solubilized cesium; and separating the predetermined cesium compound. A drilling fluid or heavy medium separation fluid comprising the predetermined cesium compound of the process and having a specific gravity of between about 1.2 $g/cm^3$ and about 2.5 $g/cm^3$ and having less than 85% by weight of the predetermined cesium compound on a solution basis is also disclosed.

10 Claims, 4 Drawing Sheets

U.S. PATENT DOCUMENTS

| | | | |
|---|---|---|---|
| 3,130,010 A | 4/1964 | Moolenaar et al. | |
| 3,175,610 A | 3/1965 | Osoba | |
| 3,207,571 A | 9/1965 | Berthold et al. | |
| 3,208,518 A | 9/1965 | Patton | |
| 3,382,229 A | 5/1968 | Patton | |
| 3,382,924 A | 5/1968 | Veley et al. | |
| 3,489,509 A | 1/1970 | Johnson | |
| 3,554,287 A | 1/1971 | Eilers | |
| 3,581,824 A | 6/1971 | Hurd | |
| 3,618,665 A | 11/1971 | Fulford | |
| 3,766,983 A | 10/1973 | Chiu | |
| 3,779,935 A | 12/1973 | McDougall et al. | |
| 3,889,753 A | 6/1975 | Richardson | |
| 3,953,340 A | 4/1976 | Templeton et al. | |
| 3,960,832 A | 6/1976 | Kang et al. | |
| 3,977,472 A | 8/1976 | Graham et al. | |
| 3,999,607 A | 12/1976 | Pennington et al. | |
| 4,048,079 A | 9/1977 | Clampitt et al. | |
| 4,118,441 A | 10/1978 | Le Blanc | |
| 4,142,595 A | 3/1979 | Anderson et al. | |
| 4,164,979 A | 8/1979 | Nooner | |
| 4,257,972 A | 3/1981 | Vidal et al. | |
| 4,371,443 A | 2/1983 | Keeney | |
| 4,427,556 A | 1/1984 | House et al. | |
| 4,440,649 A * | 4/1984 | Loftin et al. | 507/140 |
| 4,447,406 A | 5/1984 | Mein | |
| 4,466,950 A | 8/1984 | Mein | |
| 4,469,670 A | 9/1984 | Mein | |
| 4,515,700 A | 5/1985 | Hitzman | |
| 4,519,923 A | 5/1985 | Hori et al. | |
| 4,532,052 A | 7/1985 | Weaver et al. | |
| 4,536,297 A * | 8/1985 | Loftin et al. | 507/140 |
| 4,565,647 A | 1/1986 | Llendado | |
| 4,597,955 A | 7/1986 | Mein | |
| 4,606,764 A | 8/1986 | Hazen et al. | |
| RE32,556 E | 12/1987 | Mein | |
| 4,725,311 A | 2/1988 | Krennrich et al. | |
| 4,855,069 A | 8/1989 | Schuppiser et al. | |
| 4,900,457 A * | 2/1990 | Clarke-Sturman | 507/145 |
| 4,938,934 A | 7/1990 | Pillai et al. | |
| 5,105,887 A | 4/1992 | Hewgill et al. | |
| 5,605,669 A | 2/1997 | Hofmann et al. | |
| 5,804,535 A * | 9/1998 | Dobson et al. | 507/145 |
| 5,881,826 A * | 3/1999 | Brookey | 507/145 |
| 6,017,856 A * | 1/2000 | Van Ooyen | 507/145 |
| 6,123,159 A * | 9/2000 | Brookey | 507/140 |
| 6,124,244 A * | 9/2000 | Murphey | 507/140 |

FOREIGN PATENT DOCUMENTS

| | | |
|---|---|---|
| DE | 1 253 252 | 11/1967 |
| DE | 26 51 228 | 5/1978 |
| DE | 42 37 954 | 4/1994 |
| DE | 43 13 480 | 4/1994 |
| DE | 43 39 062 | 2/1995 |
| EP | 0 131 206 | 1/1985 |
| EP | 0 132 656 | 2/1985 |
| EP | 0 137 872 | 5/1987 |
| EP | 0 495 579 | 7/1992 |
| EP | 0 259 939 | 4/1993 |
| EP | 0 572 113 | 12/1993 |
| EP | 0 621 329 | 10/1994 |
| GB | 987 840 | 3/1965 |
| GB | 2 265 924 | 10/1993 |
| GB | 2 277 338 | 10/1994 |
| PL | 177619 | 2/1996 |
| SU | 1546-425 | 2/1990 |
| WO | WO 87/03898 | 7/1987 |
| WO | WO 94/09253 | 4/1994 |
| WO | WO 94/25422 | 11/1994 |
| WO | WO 95/21900 | 8/1995 |

OTHER PUBLICATIONS

Ramsey Et Al., IADC/SPE 36398, pp. 263–272, 1996.*

"Cesium and Cesium Compounds", p. 331, 335–336, Kirk–Othmer Encyclopedia of Chemical Technology Third Ed., vol. 5, (1979).

Conners, "Use of Cleark Brine Completion Fluids as Drill-in Fluids", Sep. 1979, SPE 8223.

Darlington, "Viscous Heavy Brine Completion Fluids", Mar. 1982, SPE–10671.

Degouy, "Design of Environmentally Safe Drilling Fluids: Tests Under Actual Bottomhole Conditions in an Original Flow Loop", Sep. 1991, SPE 23063.

Doty, "Clear Brine Drilling Fluids: A Study of Penetration Rates, Formation Damage, and Wellbore Full–Scale Drilling Tests", 1985 p. 167–175, SPE/IADC 13411.

Downs et al., "Development of Environmentally Benigh Formate–Based Drilling and Completion", Nov. 1993, Shell Publication No. 1194, SPE 27143.

Downs, "Formate Brine: New Solutions to Deep Slim–Hole Drilling Fluid Design Problems", Nov. 1992, SPE 24973.

Downs, "Formate Brines—Novel Drilling and Completion Fluids for Demanding Environments", Oct., p. 3–13, Shell Publication No. 1137, SPE 25177, (1992).

Downs, "TAME: A New Concept in Water Based Drilling Fluids for Shales", Sep. 1993, SPE 26699.

Heindl, "Cesium", 1970, p. 527–534, Bureau of Mines Bulletin 650, Mineral Facts and Problems 1970 Edition.

Howard, "Formate Brines for Drilling and Completion: State of the Art", Oct. 1995, SPE 30495.

Kemp et al., "Density Modeling for Pure and Mixed–Salt Brines as a Function of Composition, and Pressure", 1987, p. 253–265, SPE/IADC 16079.

Kemp, "Mutual Solubility of Salts in Drilling and Completion Fluids", 1987, p.351–362, SPE 16688.

Kennedy, "The Alkali Metal Cesium and Some of its Salts", Jan. 1938, p. 157–163, Chemical Reviews 23 (1938).

Kilbourn, "Cesium and Cesium Compounds", 1993, p. 749–763, Kirk–Othmer Encyclopedia of Chemical Technology Fourth Ed., vol. 5 North, "Research Uses Its Brines!", Feb. 1993, p. 33–35, Shell World.

Paul, "Solids Free Completion Fluids Maintain Formation Permeability", Sep. 1973, SPE 4655.

Thomas, "Pressure and Temperature Effects on Brine Completion Fluid Density", Feb. 1984, SPE 12489.

Wendorff, "New Solids–Free, High Density Brines Solve Many Workover and Completion Problems", Feb. 1974, SPE 4788.

Williams et al., "Acidizing Fundamentals", 1979, p. 3, 10–12, 16, 20, 23, 34–35, 83–84, 95, Henry L. Doherty Memorial Fund of AIME, Society of Petroleum Engineers of AIME.

Worrall, "An Evolutionary Approach to Slim–Hole Drilling, Evaluation, and Completion", Feb. 1992, SPE 24965.

* cited by examiner

PROCESS FOR PRODUCING A PREDETERMINED CESIUM COMPOUND

This application is a continuation of U.S. application Ser. No. 08/858,758, filed May 19, 1997, now U.S. Pat. No. 6,015,535, which is a con. of U.S. application Ser. No. 08/417,562, filed Apr. 6, 1995, now abandon.

FIELD OF THE INVENTION

The present invention relates to the production or recovery of cesium from cesium-containing materials, and more particularly to a process for recovering cesium from cesium-containing materials in the form of a predetermined cesium compound such as a cesium salt.

BACKGROUND OF THE INVENTION

Processes for recovering cesium from cesium-containing materials such as pollucite and other cesium-containing minerals have been reported in the technical literature.

One process which is reported involves leaching ground pollucite ore with strong sulfuric acid to obtain an extract containing cesium alum, which is recovered by crystallization.

Cesium alum is cesium aluminum sulfate hydrate. Its formula can be empirically expressed as $CsAl(SO_4)_2 \cdot 12H_2O$, or $Cs_2SO_4 \cdot Al_2(SO_4)_3 \cdot 24H_2O$. The cesium alum contained in or crystallized from the sulfuric acid extracts of pollucite is typically contaminated with other metal ions such as rubidium, sodium, potassium, magnesium, and iron.

The cesium alum is then redissolved in water at an elevated temperature and reacted with an alkaline earth metal hydroxide, such as barium hydroxide or calcium hydroxide, to form an aluminum hydroxide precipitate together with precipitated barium sulfate or calcium sulfate. The cesium alum may alternatively be reacted with ammonia to precipitate the aluminum as aluminum hydroxide. The cesium sulfate remains in the supernatant solution. The cesium can be recovered from the supernatant solution and converted into other cesium compounds.

U.S. Pat. No. 3,207,571 to Berthold discloses an improved process for producing cesium compounds from cesium aluminosilicate ore. In the process disclosed by Berthold, finely ground pollucite ore and the stoichiometric quantity of sulfuric acid required for reaction with the alkali metals and aluminum present in the ore are heated to a temperature of about 150° Celsius for a period of about four hours, and a weight of water equal to one-fourth the weight of the pollucite ore used is added to the ore-acid mixture during the heating period to substantially completely extract the cesium from the ore as cesium alum. The mixture is filtered and the filtered cesium alum is then crystallized a number of times. The crystallized cesium alum is then added to a hot slurry of calcium hydroxide in distilled or demineralized water to yield a solution of cesium sulfate and a solid residue of calcium sulfate hydrate and aluminum hydroxide. The calcium hydroxide is added to the cesium alum in a quantity stoichiometrically sufficient to convert all of the cesium alum to cesium sulfate and aluminum hydroxide. The insoluble substances are separated from the cesium sulfate solution.

Berthold discloses that cesium sulfate can be recovered by evaporating the solution to dryness and calcining the salt so obtained at about 300° Celsius to remove the last traces of water. Conversion of cesium sulfate to other cesium salts can be accomplished by adding an aqueous barium hydroxide mixture to the cesium sulfate liquor. The resulting mixture is then separated to yield a solution of cesium hydroxide. Berthold provides that the cesium hydroxide can be converted to a desired cesium salt by acidification with the desired acid. To obtain a salt other than the sulfate or hydroxide, Berthold alternatively mentions treating the cesium sulfate solution with the barium salt of the desired acid.

German Patent DE 43 13 480 of Hoffmann et al. discloses a process which avoids the use of barium compounds in the production of cesium salts from cesium alum. Cesium alum is reacted with calcium hydroxide, in an amount which is equimolar to the aluminum, and with a highly water soluble calcium salt, in an amount which is equimolar to the cesium. This process results in a product containing soluble calcium sulfate and magnesium.

One known use for cesium compounds is in high specific gravity drilling fluids for oil and gas wells. Bore hole turnings are known to slow or stop the drilling process, and in some cases, plug the porous strata of the bore hole. Feedback data on the bore hole condition is limited in the regions of plugged strata thereby reducing the effectiveness of the drilling operation. Another problem which may occur is the incompatibility of impurities found in cesium compounds with the various solutions, viscosifiers, and additives used in drilling fluids. For example, the presence of divalent impurities like calcium in cesium compounds may degrade the polymers present in the viscosifiers. The presence of divalent impurities is particularly harmful in high temperature and high pressure applications commonly found in deep well drilling where the viscosifier functions to suspend the bore hole turnings and act as a drilling lubricant. High density fluids having a specific gravity of about 1.8 and above have been used to convey the turnings to the surface. For wells having a depth greater than one mile, zinc bromide and mixtures with other salts have been utilized to improve the performance of the fluids. However, the nature of these materials renders them somewhat undesirable. One material which has been defined as a replacement for zinc bromide is cesium formate. Blends of cesium formate with other alkali metal formates are also known. See European Pat. No. 572 113.

Cesium salts produced by the above described processes, however, do not avoid the problem of side reaction precipitates formed between divalent and multivalent cationic impurities and the carbonates present in the drilling environment or the corrosion effect of drilling equipment materials caused by sulfate and chloride ion impurities. In addition, the processes described above are relatively difficult and expensive for commercial application.

Therefore, there has been a recognized need for a cesium compound having a substantially reduced level of divalent and multivalent cation impurities and sulfate and chloride ions and an improved process for its preparation.

SUMMARY OF THE INVENTION

In accordance with the present invention, there is provided a method for producing a predetermined cesium compound comprising: treating a cesium-containing material with a suitable reagent to dissolve at least a portion of the cesium contained in the material and form a slurry; adding a base comprising slaked lime or calcium carbonate and a quantity of an acid containing the anion of the predetermined cesium compound to the slurry; and separating the predetermined cesium compound. As used herein, the term "predetermined cesium compound" means the compound produced by combination of free cesium ion and an anion.

In accordance with another aspect of the present invention, there is provided a method for producing a predetermined cesium compound from an ore comprising cesium aluminosilicate comprising: treating an ore comprising cesium aluminosilicate with an acid to dissolve at least a portion of the cesium contained in the ore and form a slurry; adding a base comprising slaked lime or calcium carbonate and a quantity of an acid containing the anion of the predetermined cesium compound to the slurry comprising dissolved cesium; and separating the predetermined cesium compound.

In accordance with yet another embodiment of the present invention there is provided a fluid comprising a cesium compound and having a specific gravity of between about 1.2 g/cm$^3$ and about 2.5 g/cm$^3$ and having 10% to 100% by weight of the cesium compound on a dry salt basis, and less than 85% by weight of the cesium compound on a solution basis.

Further details relating to the present invention are described in the following Detailed Description of the Invention.

DETAILED DESCRIPTION OF THE INVENTION

The present inventors have found an improved process for preparing cesium compounds useful in drilling fluids from cesium containing materials, including naturally occurring minerals or ores, such as pollucite, solutions including cesium aluminum sulfate, and other materials, e.g., spent catalysts or residues comprising cesium fluoride or cesium sulfate.

One method of the present invention comprises treating a cesium-containing material with a suitable reagent to dissolve at least a portion, and preferably all or nearly all, of the cesium contained therein and form a slurry, adding a base comprising slaked lime or calcium carbonate and an acid containing the anion of the predetermined cesium compound to the slurry comprising dissolved cesium, and separating the predetermined cesium compound from the mixture.

The method of the present invention may be carried out utilizing conventional industrial scale mixing vessels and equipment for handling the cesium-containing materials (e.g., ores) and strong acid and base solutions. The choice of the particular equipment utilized to practice the method of the invention is believed to be within the skill of one of ordinary skill in the art and therefore is not described below.

Figure 1:
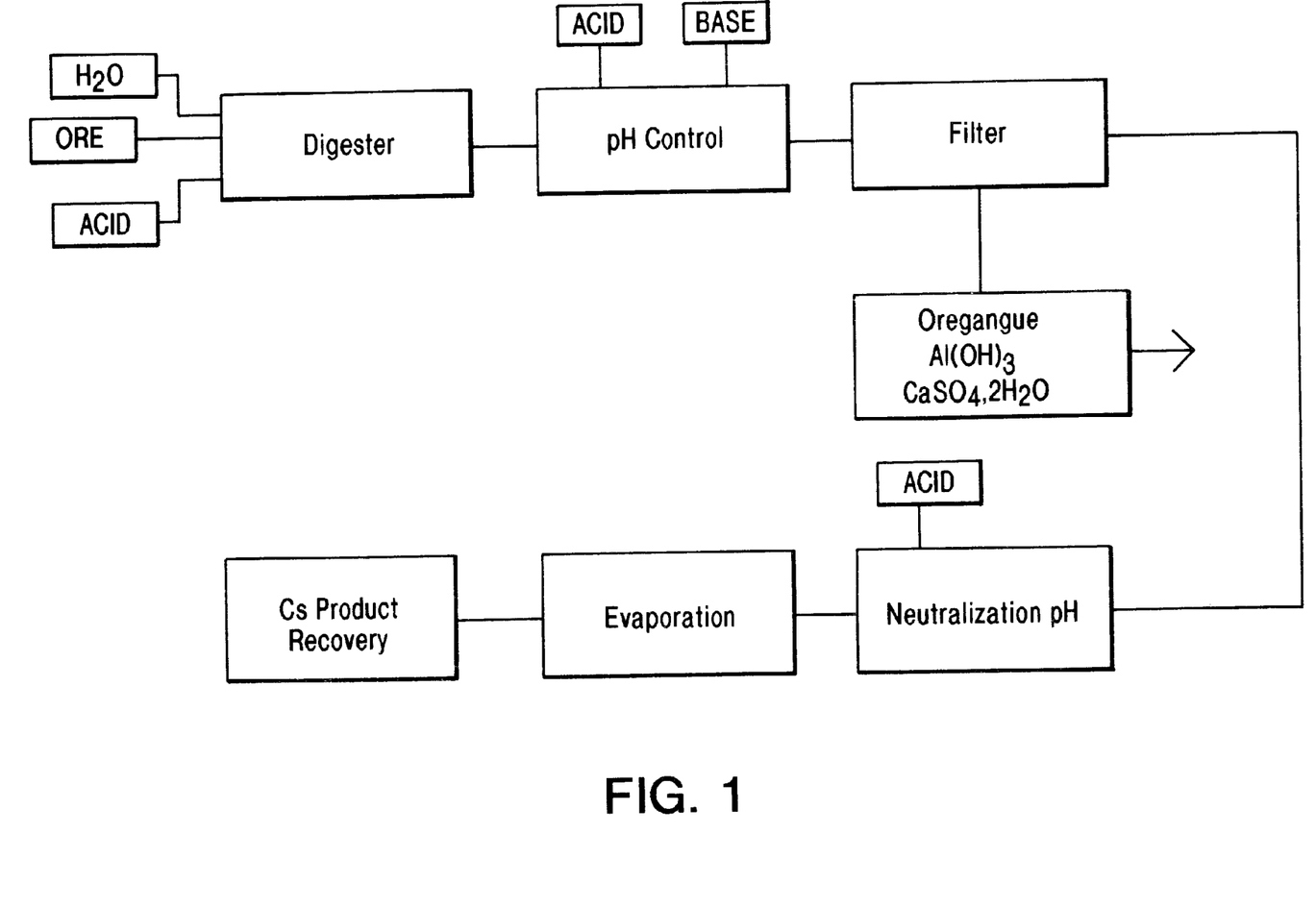
FIGS. 1 and 3 illustrate block schematic representations of alternative embodiments of a method of the invention.

With reference to an embodiment of the invention illustrated in FIG. 1, a cesium-containing material, such as pollucite ore, and an acid suitable for digesting the ore and dissolving at least the cesium present therein are combined to form a slurry. Suitable acids include, but are not limited to, mineral acids (e.g., sulfuric acid) and hydrofluoric, hydrobromic, and hydrochloric acids. Water may also be added to assist in the dissolution of the cesium and any aluminum and other alkali metals that may be present in the ore. To further assist in dissolving the cesium and any other alkali metals and aluminum in the ore, the ore may be comminuted prior to its being combined with the acid. In a preferred embodiment, the ore is ball milled to an approximately −200 mesh particle size.

In one preferred embodiment the amount of acid mixed with the ore is equal to or in excess of the stoichiometric amount of acid theoretically required to dissolve all of the cesium and any aluminum and/or other alkali metal(s) present in the ore. (The cesium, aluminum, and alkali metal content of the ore can be adequately determined by assaying the ore.) In another preferred embodiment of the process of the present invention, a 45% (by weight) solution using 93% (by weight) sulfuric acid is employed in a ratio of between 0.2 to 0.8 in kilos of ore per liters of acid solution.

As will be appreciated by those skilled in the art, the acid used to form the slurry may be a single acid or a mixture of acids. The amount of acid and/or the choice of the acid or acid mixture is dependent on the composition of the ore or residue material from which cesium is being extracted. While the following examples and discussions refer to pollucite ore, as used herein, the term "cesium-containing materials" shall include any naturally occurring cesium-containing minerals or ores, as well as other solids or liquid materials comprising cesium, including process residues such as spent catalyst material.

In a most preferred embodiment, cesium alum is formed as an intermediate in the process. Formation of the cesium alum intermediate requires the presence of sulfate ions and aluminum ions. If the acid or acid mixture does not include sulfuric acid, a source of sulfate ions can be added to facilitate the formation of a cesium alum intermediate. If the cesium-containing material does not include aluminum, a source of aluminum ions can be added to facilitate cesium alum formation.

Figure 2A:
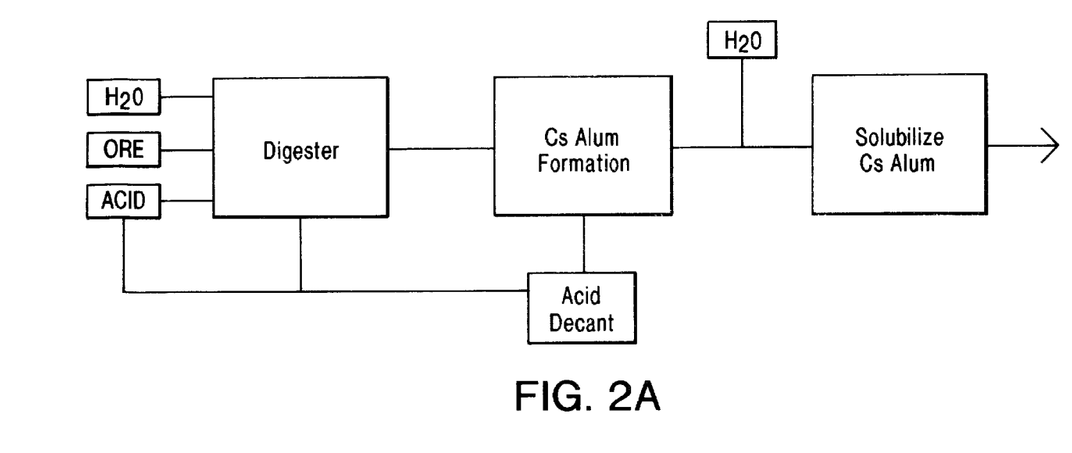
FIGS. 2A–2C illustrate block schematic representations of alternative embodiments of various aspects of a method of the invention.

As shown in FIG. 2A, the acid may be recycled into the ore digestion vessel which will reduce the amount of acid that is used.

The digestion of the ore and acid mixture is preferably conducted under conditions and for a time period sufficient to extract a sufficient amount of cesium from the ore to render the overall process commercially efficient. More preferably, the reaction is permitted to continue until at least approximately 90% of the cesium is dissolved from the ore, as may be determined from analysis of the spent ore. In one preferred embodiment of the invention, the reaction of the ore and acid is conducted with hot sulfuric acid at a temperature of from about 115° C. to about 200° C., and more preferably at a temperature of approximately 120° C. The reaction (or digestion) period is preferably at least 4 hours, and more preferably approximately 16 hours. When a shorter digestion period or a lower sulfuric acid temperature is employed, cesium dissolution from the ore is less complete. During the reaction, the hot digestion liquor becomes increasingly more paste like in consistency. Additional water may be added to maintain the original volume of the mixture. If the evaporated water is not replaced the slurry will eventually solidify. Optionally the original volume of the mixture can be maintained by refluxing. When aluminum is present in the ore, the dissolved cesium exists in a slurry of the ore with sulfuric acid as solubilized cesium aluminum sulfate (also referred to herein as cesium alum). When an excess of acid is present after achieving the desired level of digestion, the slurry may optionally be diluted with water and cooled to approximately 30° C. to crystallize cesium alum. The remaining sulfuric acid in the mixture is preferably decanted and recycled; and the remaining spent ore and cesium alum can optionally be reslurried. (See again FIG. 2A).

Reslurrying may be accomplished by adding water to the spent ore and cesium alum. The solubility of the cesium alum in the reslurry is primarily a function of water volume and temperature employed and therefore the conditions for recrystallizing the cesium alum may be readily determined by those skilled in the art. In a preferred embodiment, the temperature of the reslurry after water addition is approximately 100° C.

In accordance with the invention, the spent ore or undissolved portion of the cesium-containing material is utilized as a filtration aid for separation of aluminum hydroxide which is formed by the addition of base to the acid digested ore or treated cesium-containing material. The use of the spent ore or undissolved material improves the filtration rate of the aluminum hydroxide that is formed as well as easing the washability of the solids to maximize cesium recovery. It has been demonstrated by centrifugal spin tests that inclusion of the spent ore improves filterability, washability, compressibility, and dewatering of solids.

Figure 2B:
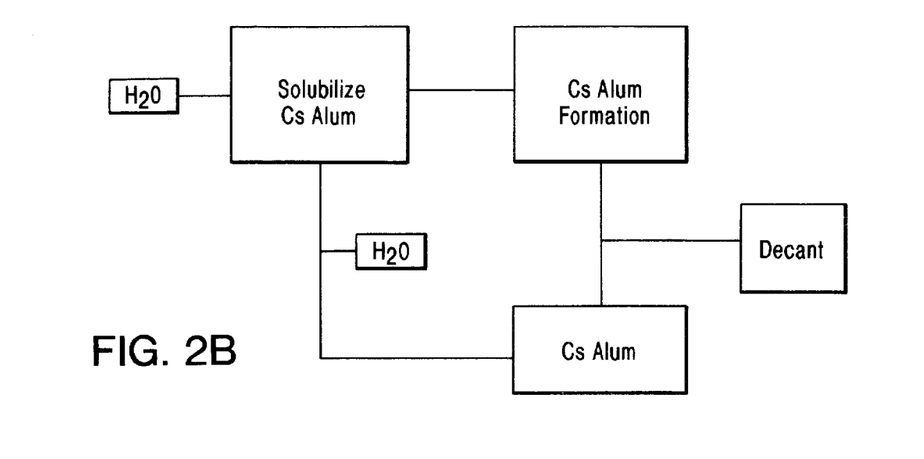

Referring to FIG. 2B, those of ordinary skill in the art will recognize that cesium alum and ultimately the predetermined cesium compound may be further purified at this point in the process by recrystallizing the solubilized cesium aluminum sulfate in the slurry for further processing. The recrystallization process may be repeated as many times as desired to further purify the cesium alum.

Referring again to FIG. 1, a base comprising slaked lime or calcium carbonate and an acid containing the anion of the predetermined cesium compound are added to the slurry and spent ore, either together or sequentially in either order, to adjust the pH to about 4 to about 9. The slaked lime is prepared by contacting lime (calcium oxide) with water ("slaking"). The "slaking" reaction is provided by equation (1).

$$CaO + H_2O \rightarrow Ca(OH)_2 \qquad (1)$$

The present inventors have discovered that there are a number of problems associated with adding lime as a base material without slaking beforehand. While not wishing to be bound by theory, it is believed that the reaction of lime with water in the slurry proceeds in a manner which slowly raises the pH above 9 and accordingly causes aluminum hydroxide to solubilize. By preslaking the lime, the pH can be controlled so that the level of aluminum and calcium impurities in the solubilized cesium compound are minimized.

In a preferred embodiment, the base comprises slaked lime. The slaked lime is allowed to react with the slurry and acid under conditions sufficient, and for a sufficient time period, to allow precipitation of the aluminum as aluminum hydroxide ($Al(OH)_3$), and to allow precipitation of any silica and/or iron dissolved in the liquid component of the slurry. As provided above, to achieve the precipitation of the aluminum hydroxide, sufficient base is added to the mixture to achieve a pH in the range of about 4 to about 9. In a more preferred embodiment, base is added to achieve a pH of about 7 to about 8. In this more preferred pH range, substantially complete precipitation of solubilized aluminum is obtained.

After the slaked lime is added, the spent ore, precipitated aluminum hydroxide, and precipitated calcium sulfate are separated from the mixture containing the solubilized cesium ions. The separation may be accomplished by any known means, such as by filtering.

In another preferred embodiment, slaked lime and calcium carbonate are employed together. The slaked lime and calcium carbonate whether used alone or in combination, may also be used with one or more additional bases comprising an ion of a metal selected from groups 1A (alkali metals) and 2A (alkaline earth metals) of the Periodic Table of the Elements and mixtures thereof. Examples of such additional bases include KOH, NaOH, $K_2CO_3$, $Na_2CO_3$, RbOH, $Rb_2CO_3$, LiOH, $Li_2CO_3$, $Mg(OH)_2$, $MgCO_3$, $Cs_2CO_3$, and CsOH.

The selection of the acid used to produce the predetermined cesium compound and the selection of the base which are added to the slurry (and any optional reslurry) depends on the particular cesium compound(s) desired. For example, if one desires to produce cesium nitrate, a combination of slaked lime and nitric acid are added in an amount sufficient to adjust the pH of the mixture to approximately 7 to 8. It is believed that the reaction proceeds according to equation (2) and that similar reactions will occur with other acids:

$$CsAl(SO_4)_2 + 2Ca(OH)_2 + HNO_3 + 3H_2O \rightarrow CsNO_3 + Al(OH)_3 + 2CaSO_4 \cdot 2H_2O \qquad (2)$$

Examples of acids suitable for use in preparing a predetermined cesium compound (or cesium salt), include but are not limited to the acids set forth in Table 1:

TABLE 1

Acids/Cesium Compounds

| Acid Added | Cesium Compound Product |
|---|---|
| Nitric Acid ($HNO_3$) | Cesium Nitrate ($CsNO_3$) |
| Formic Acid (HCOOH) | Cesium Formate (CsCOOH) |
| Formic Acid (as calcium formate) ($Ca(OOCH)_2$) | Cesium Formate (CsCOOH) |
| Hydrochloric Acid (HCl) | Cesium Chloride (CsCl) |
| Hydrobromic Acid (HBr) | Cesium Bromide (CsBr) |
| Acetic Acid ($HC_2H_3O_2$) | Cesium Acetate ($CsC_2H_3O_2$) |
| Hydroiodic Acid (HI) | Cesium Iodide (CsI) |

As will be recognized by those of ordinary skill in the art, Table 1 provides a list of examples of acids that can be used and is not to be construed as a complete or exhaustive list of suitable acids. Rather, suitable acids include any acids which will react with the cesium ions to yield the cesium compound desired as the end product.

As will also be recognized by those of ordinary skill in the art from Table 1, it is possible to substitute certain salts for the acid. For example, as shown, calcium formate may be added instead of formic acid to produce a cesium formate end product.

Figure 2C:
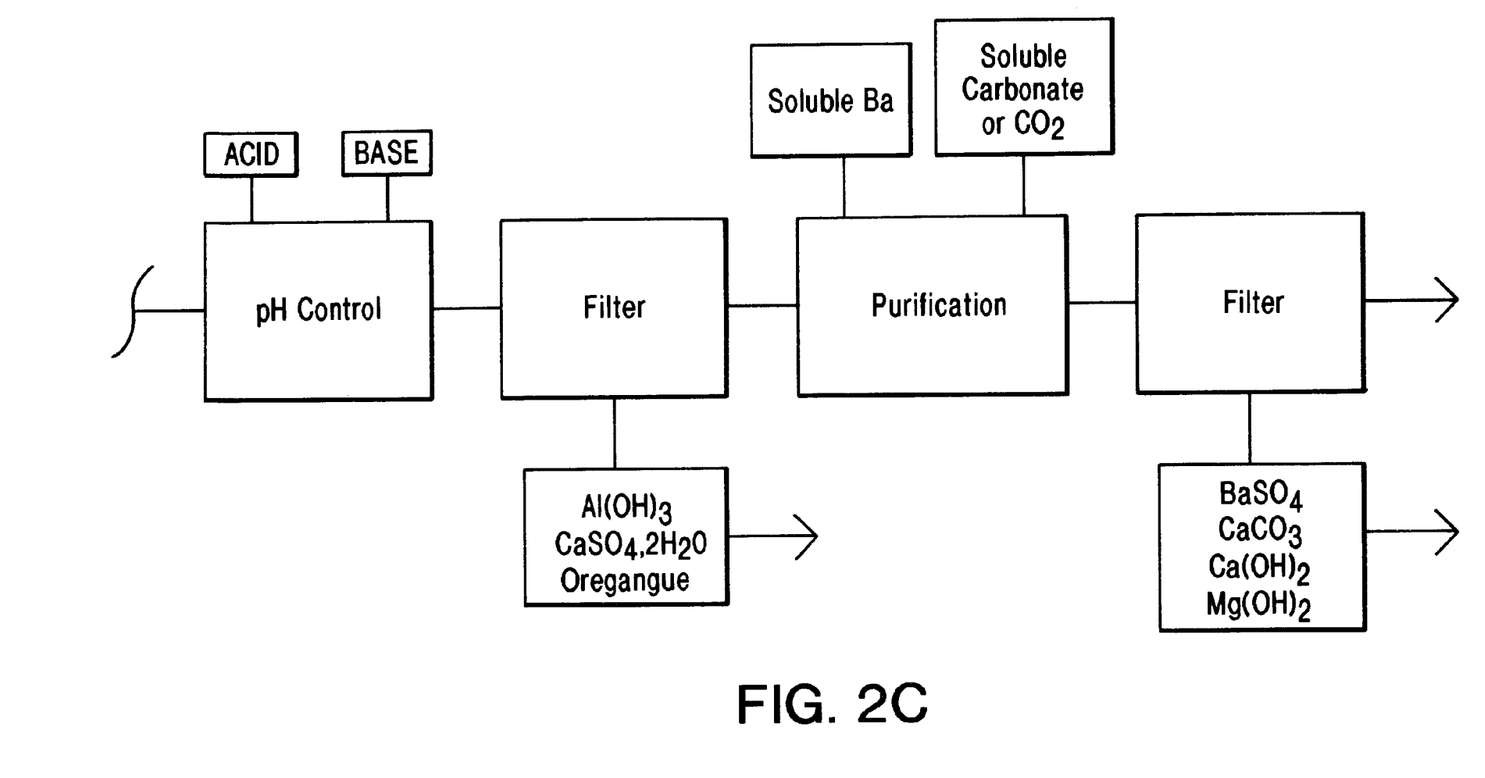

Referring to FIG. 2C, as part of the separation and recovery step, the solubilized cesium compound may be optionally purified or "polished" to remove trace impurities. As depicted in FIG. 2C, soluble compounds of barium and soluble compounds of carbonate (or carbon dioxide) may be added to the solution mixture containing solubilized ions of cesium and the anion of the predetermined cesium compound. Typically, for purposes of polishing, less than 0.12 kilogram of barium hydroxide is added per 1 kilogram of cesium compound contained in the solution. Insoluble barium sulfate, calcium hydroxide, and magnesium hydroxide formed as a result of the polishing step may be removed by filtration. Residual calcium ions in solution may be removed through the addition of alkali carbonates such as cesium carbonate, potassium carbonate, or sodium carbonate, or by treatment with carbon dioxide, to precipitate insoluble calcium carbonate. The alkali carbonate is employed in an amount sufficient to precipitate all calcium ions present in the solution mixture. The extent to which the purification of the predetermined cesium compound is carried out is dependent on the end use application for the cesium compound.

After polishing, the solution containing the dissolved cesium compound has an elevated pH of greater than 11. In order to improve the recovery of the cesium compound, an additional quantity of acid (of the type employed to form the predetermined cesium compound) is added to adjust the pH of the solution to a desired pH. The desired pH is dependent upon intended use or application. The cesium compound may then be recovered or separated, e.g., by driving off the water through heating.

In the process of the invention, the predetermined cesium compound can be recovered as a solid or in solution, or as a solid or solution mixture including the predetermined cesium compound and one or more compounds comprising a different metal (e.g., alkali metals) and the anion of the predetermined cesium compound.

Figure 3:
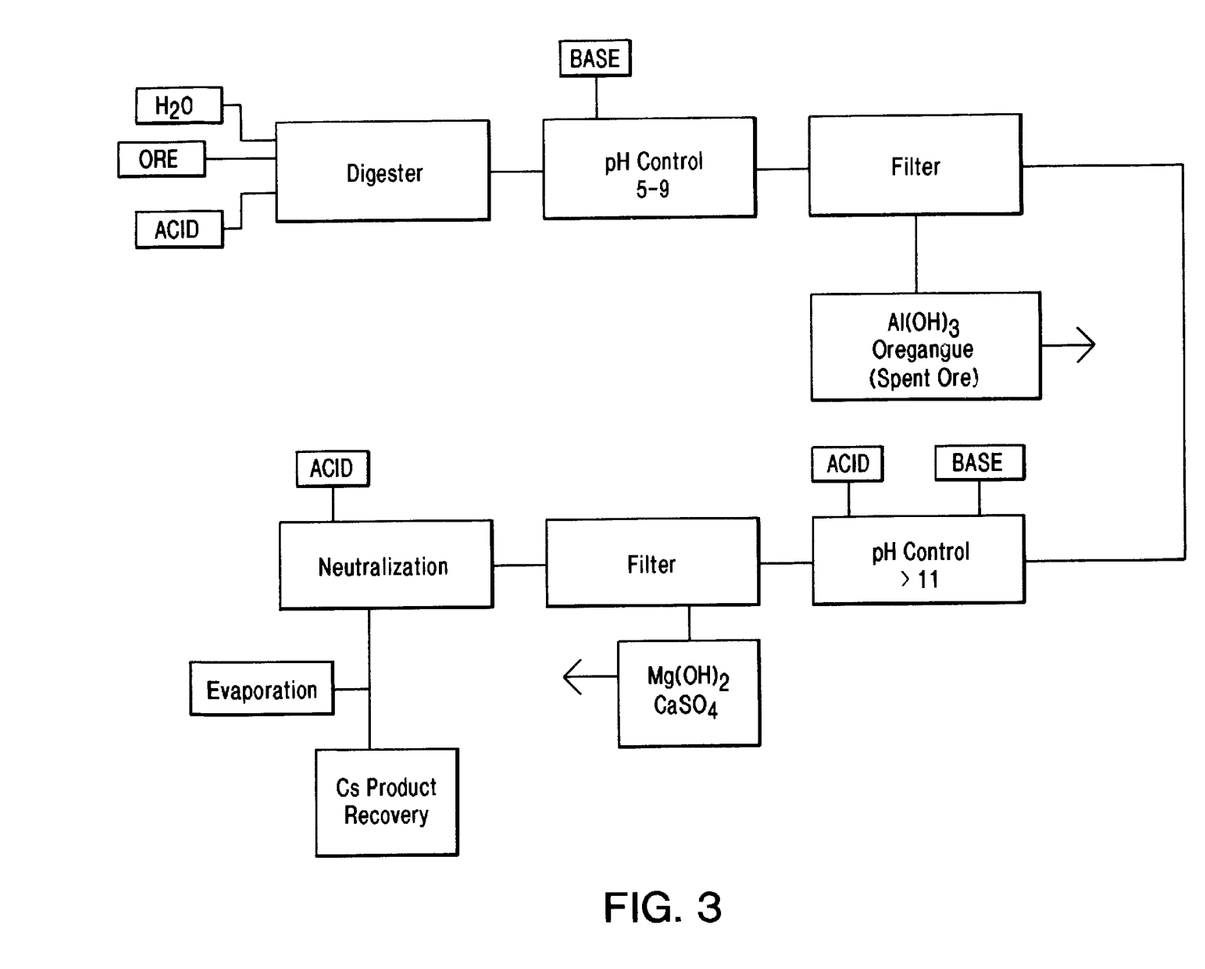

Referring now to FIG. 3, there is illustrated an embodiment of the present invention wherein the base comprising slaked lime or calcium carbonate and acid containing the anion of the predetermined cesium compound are added after the ore/acid digestion slurry has been treated with a first quantity of base. As discussed above and illustrated in FIG. 1, ore which has been preferably ground to a mesh of −200, is mixed or contacted with a suitable acid (e.g., sulfuric acid) and water in a process tank for dissolution of cesium and aluminum from the ore. The quantity of acid utilized in this step is preferably at least a stoichiometric quantity with respect to group 1A elements of the Periodic Table of Elements and aluminum contained in the ore. Water may be added to maintain the original volume. While not shown, the embodiment of the invention illustrated in FIG. 3 may further include cooling the hot digestion slurry to obtain cesium alum and spent ore to crystallize the cesium alum, decanting the supernatant liquid which may include excess unreacted acid, and reslurrying the crystallized cesium alum and spent ore in water. Even if no excess acid is present, the crystallization and reslurry steps may be performed.

Referring again to FIG. 3, the first quantity of base is mixed with the hot digestion slurry or alternatively, with the reslurry of cesium alum and spent ore, to adjust the pH to about 4 to about 9. The base comprises an ion of a metal selected from groups 1A and 2A of the Periodic Table of the Elements (e.g., slaked lime, calcium carbonate, lime, potassium hydroxide, sodium hydroxide, potassium carbonate, sodium carbonate) and mixtures thereof. The base is allowed to react with the slurry or alternatively, the reslurry under conditions sufficient, and for a sufficient time period, to allow precipitation of the aluminum as aluminum hydroxide $(Al(OH)_3)$; to allow precipitation of any silica and iron dissolved in the slurry or reslurry and to allow the formation of solubilized cesium sulfate. It is believed that the precipitation generally proceeds according to the reaction illustrated in equation (3):

$$2CsAl(SO_4)_2 + 3Ca(OH)_2 + 6H_2O \rightarrow 2Al(OH)_3 + 3CaSO_4 \cdot 2H_2O + Cs_2SO_4 \quad (3)$$

After the addition of slaked lime and the formation of solubilized cesium sulfate, the principal undissolved solids, e.g., precipitated aluminum hydroxide, precipitated calcium sulfate, and spent ore, are separated from the liquid component of the mixture. The liquid component includes crude cesium sulfate. The separation may be accomplished by any means known to the art, such as by filtering.

The inventors have discovered that the spent ore facilitates the filtering, washing, and dewatering characteristics of the precipitated $Al(OH)_3$ and $CaSO_4 \cdot 2H_2O$ cake much like the enhanced filter throughput achieved by adding granular silica as a filtering aid.

A second base comprising slaked lime or calcium carbonate and an acid containing the anion of the predetermined cesium compound are then added to the solubilized cesium sulfate. The reaction mechanism proceeds in accordance with the mechanism identified in equation (4) below:

$$Cs_2SO_4 + 2HCOOH + CaO + H_2O \rightarrow 2CsCOOH + CaSO_4 \cdot 2H_2O \quad (4)$$

A slight excess of slaked lime can be added to achieve a pH sufficient to precipitate as magnesium hydroxide at least a portion, and preferably all or nearly all, of any trace quantities of soluble magnesium present in the mixture to facilitate its removal by known separation techniques.

The acid is selected to contain the anion of the cesium compound desired as an end product. Examples are set forth in Table 1.

The second base may further include base(s) comprising an ion of a metal selected from groups 1A and 2A of the Periodic Table of the Elements and mixtures thereof. For example, the second base may comprise slaked lime or calcium carbonate, or slaked lime and/or calcium carbonate and one or more of the following bases: potassium hydroxide, sodium hydroxide, potassium carbonate and sodium carbonate.

To further purify the cesium compounds obtained by this embodiment, the polishing steps illustrated in FIG. 2C, may optionally be employed in the same manner as discussed above.

After polishing, the solution containing the dissolved cesium compound has an elevated pH of greater than 11. In order to improve the recovery of the cesium compound, an additional quantity of acid (of the type employed to form the predetermined cesium compound) is added to adjust pH of the solution to a desired pH. The desired pH is dependent upon intended use or application. The cesium compound may then be recovered or separated e.g., by driving off the water through heating.

In the process of the invention, the predetermined cesium compound can be recovered as a solid or in solution, or as a solid or solution mixture including the predetermined cesium compound and one or more compounds comprising a different metal (e.g., alkali metals) and the anion of the predetermined cesium compound.

A range of cesium compounds of varying composition and purity produced in accordance with the present invention are suitable for use as drilling fluids or heavy medium separation fluids. Alternatively, salts of other metals such as sodium or potassium can be coformed with the predetermined cesium compounds by adding such ions to the solution mixtures comprising solubilized cesium at any step of the process. For example, in one embodiment, a cesium formate is produced by the process of the invention and sodium formate or potassium formate are co-formed therewith in order to produce a mixed salt product. The composition of the salt or salt mixture produced is dependent on the anion of the acid and cation(s) of the base(s) utilized and the amounts thereof which are reacted with the solubilized cesium sulfate or with the solubilized cesium alum.

In accordance with another aspect of the invention there is provided a high specific gravity fluid which comprises an aqueous mixture on a dry salt basis of between 10 and 100% of a cesium compound produced in accordance with the present invention. The high specific gravity fluid produced has varied applications including use as a drilling fluid or in mineral extraction processes. The high specific gravity fluid contemplated by this invention has a specific gravity of between 1.2 g/cm³ and about 2.5 g/cm³ and on a dry salt basis and comprises less than 0.50% (by weight) of chloride or sulfate anions; less than 0.3% (by weight) of materials such as aluminum, barium, calcium, or magnesium containing compounds; and less than 0.2% (by weight) total of other multivalent cationic impurities. The fluids of the invention are further disclosed and represented by the following non-limiting Examples. The high specific gravity fluid may further comprise compounds of sodium or potassium where the anion of the compound is the same as that of the cesium compound included in the fluid.

Chemical analysis of the cesium compounds was performed using conventional gravimetric analysis, emissions spectrographic analysis and atomic absorption techniques, readily known to those skilled in the art.

EXAMPLE 1

This example illustrates the production of cesium formate via a one step reaction according to the present invention.

A 4 liter glass beaker was loaded with 444 grams of ground pollucite ore of nominally −200 mesh, 670 ml water, and 310 ml 98% by weight $H_2SO_4$. This represents about an 82% excess of acid above the stoichiometric requirements for dissolution of alkali metals and aluminum from the ore. The mixture was continually mixed while heating at approximately 115° C. for 16 hours. The leach volume was maintained by adding water.

After 16 hours, the slurry was diluted to a volume of 2200 ml with water, reheated to about 80–90° C., then cooled to room temperature. A decant of 940 ml was taken to remove most of the remaining unreacted $H_2SO_4$ acid. Nine hundred (900) ml of water were then added to reslurry the spent ore and crystallized cesium alum and the reslurry mixture was then heated to 80° C. with stirring.

A slurry of slaked lime, made from 185 grams of calcium oxide and 700 ml water, was added to the heated reslurry mixture of cesium alum and spent ore along with 30 ml of 88% (by weight) formic acid. After these additions, the pH of the resulting mixture was 7.5. The mixture was heated to about 70° C. and stirred for 1 hour.

The liquid component of the mixture (which contains the solubilized cesium formate) was then separated from the spent ore and the $Al(OH)_3$ and $CaSO_4$ precipitates by filtration. The filtered residue weighed 736 grams on a dry weight basis. A wash of 600 ml of boiling water was applied to the filtered solids. The filtrates containing the solubilized cesium formate were combined and mixed first with 38 grams $Ba(OH)_2.8H_2O$ to remove residual $SO_4^{-2}$; then with 15 grams $Cs_2CO_3$ to remove residual calcium ions. The solubilized cesium formate product was then filtered to separate out barium sulfate, calcium carbonate, calcium hydroxide, and magnesium hydroxide. The filtrate was then analyzed and found to contain the following chemical make-up. (Values are recorded on a part per million on a dry weight basis of cesium formate product.)

| | |
|---|---|
| Rb | 9500 ppm |
| K | 500 ppm |
| Na | 7900 ppm |
| Li | 90 ppm |
| Ca | 20 ppm |
| Cl | 500 ppm |
| $SO_4$ | <100 ppm |

-continued

| | |
|---|---|
| Al | 50 ppm |
| Ba | 50 ppm |
| Fe | 4 ppm |
| Mg | 1 ppm |

The overall extraction yield was approximately 85%.

The cesium formate containing filtrate was next mixed with a minimal amount of 88% (by weight) formic acid (less than 1 ml) to adjust the solution to a pH of from about 6 to about 7. The cesium formate filtrate was then evaporated to a final volume of 53 ml; which had a density of 2.20 g/ml (approximately 79% CsCOOH).

EXAMPLE 2

A 4 liter glass beaker was loaded with 444 grams of pollucite ground to −200 mesh, 670 milliliters (ml) water, and 310 ml 98% $H_2SO_4$. The mixture was mixed and heated to approximately 115° C. for 16 hours. The leach volume was maintained with added water.

After 16 hours, the slurry was diluted to a volume of 2200–2500 ml with water, reheated, then cooled to room temperature. A decant of 1135 ml was taken to remove most of the remaining $H_2SO_4$ acid. The remaining cesium alum plus spent ore was reslurried with approximately 800 ml water, and heated to approximately 70° C. with stirring.

A slurry of slaked lime made from 150 grams of calcium oxide in approximately 500 ml water was added and a pH of 7–8 was obtained. The slurry was mixed for 1 and 1/2 hours at 90° C., cooled to 60° C., and then filtered to separate the insoluble solids including aluminum hydroxide, calcium sulfate, and spent ore. On a dry basis, the insolubles separated from the slurry weighed 675 grams.

The resulting $Cs_2SO_4$ filtrate plus wash water was heated to 70° C., and a mixture of 20 grams of calcium oxide in 100 ml of water, and 28 ml 88% (by weight) formic acid was added with mixing. An additional slurry of 2 grams calcium oxide in minimal water was added to raise the pH to above 11.5 to precipitate magnesium hydroxide.

The mixture was heated to 70° C. and mixed for 1.5 hours, followed by filtering and washing of the collected solids with water. The cesium formate filtrate was then purified by the following steps:

The cesium formate filtrate was mixed with 20 grams $Ba(OH)_2.8H_2O$ to remove residual $SO_4^{-2}$ ions as $BaSO_4$, and then with 20 grams $Cs_2CO_3$ to remove residual calcium as $CaCO_3$. The $BaSO_4$ precipitate was filtered out prior to the treatment with $CS_2CO_3$. After the $CaCO_3$ precipitate was filtered out; the final purified or polished CsCOOH filtrate was analyzed and determined to have the following chemical make-up:

| | |
|---|---|
| Rb | 6000 ppm |
| K | 270 ppm |
| Na | 4500 ppm |
| Li | 25 ppm |
| Ca | 45 ppm |
| Cl | 415 ppm |
| $SO_4$ | <80 ppm |
| Al | 25 ppm |

-continued

| | |
|---|---|
| Fe | 5 ppm |
| Ba | 100 ppm |
| Mg | 3 ppm |

The overall extraction yield was approximately 80%.

The cesium formate filtrate was mixed with a minimal amount of 88% formic acid (by weight) (less than 1 ml) to adjust the solution to a pH of between 6 and 7. The cesium formate filtrate was evaporated to a final volume of 42 mls; which had a density of 2.34 g/ml (approximately 83% CsCOOH).

It should be clearly understood that the forms of the present invention herein described are illustrative only and are not intended to limit the scope of the invention.

What is claimed is:

1. A drilling fluid comprising:
    a cesium compound;
    less than 0.5%, by weight, of chloride and sulfate; and
    less than 0.3%, by weight, of aluminum, barium, calcium and magnesium, wherein the drilling fluid has a specific gravity between about 1.2 g/cm$^3$ and about 2.5 g/cm$^3$.

2. The drilling fluid of claim 1 wherein the cesium compound is cesium formate.

3. The drilling fluid of claim 1 further comprising less than 0.2% by weight of the total of other multivalent cationic compounds.

4. The drilling fluid of claim 2 wherein the weight ratio of cesium formate to calcium is greater than about 50,000:1.

5. The drilling fluid of claim 2 wherein the weight ratio of cesium formate to chloride is greater than about 2,000:1.

6. The drilling fluid of claim 2 wherein the weight ratio of cesium formate to sulfate is greater than about 10,000:1.

7. The drilling fluid of claim 6 wherein the weight ratio of cesium formate to sulfate is greater than about 12,500:1.

8. The drilling fluid of claim 2 wherein the weight ratio of cesium formate to the sum of calcium, aluminum, barium, iron and magnesium is greater than about 5,618:1.

9. The drilling fluid of claim 8 wherein the ratio of cesium formate to the sum of calcium, aluminum, barium, iron and magnesium is greater than about 8,000:1.

10. The drilling fluid of claim 1 wherein the weight ratio of cesium to calcium is greater than about 12,222:1.

* * * * *